United States Patent [19]

Ferriere et al.

[11] Patent Number: 4,665,317

[45] Date of Patent: May 12, 1987

[54] PROCESS AND EQUIPMENT FOR SENSING SURFACE DEFECTS ON A MOVING STRIP

[75] Inventors: Dominique Ferriere, St Germain en Laye; Bernard Giraudy, Taverny, both of France

[73] Assignees: Institute de Recherches de la Siderurgie Francaise (IRSID), St Germain en Laye; USINOR (Soc. An.), Puteaux, both of France

[21] Appl. No.: 700,365

[22] Filed: Feb. 11, 1985

[30] Foreign Application Priority Data

Feb. 10, 1984 [FR] France ............... 84 02078

[51] Int. Cl.⁴ .............................. G01N 21/89
[52] U.S. Cl. ......................... 250/562; 250/563; 358/106; 356/430
[58] Field of Search ............. 358/106, 101, 107; 250/563, 572, 562, 571; 356/429–431

[56] References Cited

U.S. PATENT DOCUMENTS

| | | | |
|---|---|---|---|
| 3,049,588 | 8/1962 | Barnett | 358/106 |
| 3,887,762 | 6/1975 | Uno et al. | 358/106 |
| 4,149,089 | 4/1979 | Idelsohn et al. | 250/563 |
| 4,221,974 | 9/1980 | Mueller et al. | 250/563 |
| 4,253,113 | 2/1981 | Decavel et al. | 358/106 |
| 4,454,545 | 6/1984 | Duschl | 358/106 |
| 4,546,384 | 10/1985 | Kowalski | 358/106 |
| 4,561,104 | 12/1985 | Martin | 358/106 |
| 4,570,180 | 2/1986 | Baier et al. | 358/106 |

FOREIGN PATENT DOCUMENTS

0058028  8/1982  European Pat. Off.

OTHER PUBLICATIONS

Feliss et al., "Surface Analyzer", *IBM Technical Disclosure Bulletin*, vol. 25, No. 4, 9/82, p. 2047.
Suresh et al., "A Real-Time Automated Visual Inspection System for Hot Steel Slabs", *IEEE Transactions on Pattern Analysis and Machine Intelligence*, vol. PAMI-5, No. 6, 11/83, pp. 563–571.

*Primary Examiner*—Edward P. Westin
*Assistant Examiner*—Charles Wieland
*Attorney, Agent, or Firm*—Pollock, Vande Sande & Priddy

[57] ABSTRACT

Images of successive portions of a surface of a strip are formed and converted as analog signals. Signals typical of each image are stored in an image storage whereas the analog signals relating to each image are converted in numerical form by splitting up the image into image elements. Each of the image elements is given a numerical value, and then filtered, in order to sense the relative variations of the numerical values of the image elements. To determine whether or not to deliver a defect-sensing signal in terms of the sensed variations, the filtered signal is scanned. The typical image is stored in response to the transmission of the defect signal. Every read-in information is stored and displayed at a check station long enough for a visual check of the image it represents.

18 Claims, 4 Drawing Figures

PROCESS AND EQUIPMENT FOR SENSING SURFACE DEFECTS ON A MOVING STRIP

FIELD OF THE INVENTION

This invention relates to sensing of surface defects on a moving strip, and more particularly, to a process of the type according to which analog signals, which represent images of successive portions of the surface of the strip are formed. These signals are processed for sensing anomalous level values.

The range of applicability of the invention relates, more particularly, to that of surface-defect sensing of a rolled strip moving at high speed.

BACKGROUND OF THE INVENTION

Within the scope of this application, a process as defined above is described in the French Pat. No. 77 27 501. The surface of the strip is illuminated and, using a television camera, reflected images of successive portions of the surface of the strip are formed thus achieving a continuous representation of the inspected surface. Each image is scanned by comparing it at peak luminance level and minimum luminance level. A recording is made of the number of sensed defects on each image and of the percentage of the total area of the defects in relation to the area of the portion of the strip corresponding to an image.

It is known that inspection of rolled strips and especially hot-rolled strips at the exit of a pickling line is no easy matter, as, on the one hand, there is a large number of potential defects, varying more or less in size, visibility or consequence and, on the other, the surface of a strip is rough and exhibits spots due to uneven pickling. That is why, using the known prior art process described above, it is virtually impossible to achieve efficient sensing of all the actual defects without bringing in a substantial portion of overdetection.

Accordingly, in actual practice, a visual inspection of the strips is resorted to, so that the operator has a clear image of the strip in motion; the speed of the latter must necessarily be restricted. Now, it it desirable to carry out an inspection of both sides of the strip at high-speed and to sense the defects in real time. This capability would be very beneficial for making possible inspection of a strip after hot rolling and pickling and prior to cold rolling, when the cold-rolling strip mill is connected direct to the pickling line. It follows in such case that the combination of reliable sensing of unacceptable defects during the cold-rolling operation and of a fast moving rate, e.g., up to 6 m/s at the check station, is highly desirable.

SUMMARY OF THE INVENTION

Therefore, the purpose of this invention is to provide a process ensuring effective sensing of surface defects on a moving strip even when the latter runs at high speed.

This goal is accomplished by a process defined at the beginning of the description and according to which:
 typical signals of each image of a portion of the inspected surface of the strip are stored in an image memory;
 the processing of the analogue signals relating to each image is carried out while such image is formed. The process includes the following operations: converting analogue-to-numerical signals by splitting up the image into image elements to each of which is associated a numerical value, filtering the numerical signals typical of the image to sense the relative variations of the numerical values of the image elements and analyzing the filtered signals to possibly deliver a defect-sensing signal in terms of the sensed variations, the stored typical image being retained in response to the transmission of the defect-sensing signal; and
 every stored image is retained and displayed at a check station long enough to make a visual check of the image it represents.

Therefore, the process according to the invention. combines reliability of automatic sensing surface unevennesses on a moving strip with reliability of the qualification of the unevennesses sensed by a visual check of the fixed images of these unevennesses. Filtering of the numerical signals typical of an image may be carried out with a contour-sensing two-way filter, e.g., by sensing, between elements adjacent to one another, variations of numerical values in amplitude higher than a first preset threshold to elaborate a quantitative information, e.g., area or perimeter, of the surface unevennesses of the relevant image and to deliver the defect-sensing signal according to whether or not this quantitative information is higher than a second preset threshold.

According to a feature of the process according to the invention, filtering of the numerical signals is performed in two different ways, according to whether these signals are associated with image elements adjacent to the edges of the strip or to image elements which are right on the strip. To do this, the numerical signals are separated into initial numerical signals typical of the image portions along the edges of the strip and in second numerical signals typical of the other portions of the image. The initial numerical signals are processed to sense the amplitude variations corresponding to the change-over from one side to the other of the edges of the strip and to deliver an information denoting the difference between the sensed position of the edge of the strip and a reference position, and the second numerical signals are processed to associate with each image element information denoting the variations in amplitude of the numerical signals associated with the adjacent image elements. In this way, the defects on the edge can be sensed by considering the difference between the measured position and position of reference of the edges, while the defects right on the strip can be sensed by seeking the image elements along the contour of a "spot" of the image.

Preferably, the signals typical of each image are stored in a mass storage which is addressable image by image, and the change-over from one address to another in the write mode is controlled in response to a defect-sensing signal.

The stored data are preferably read sequentially for displaying each image they represent during a preset time. At the end of the present time the address corresponding to the stored image which has just been displayed is again available in the write mode. In this way, a preset time is made available for the operator qualifying the sensed surface uneveness; at the end of this time the stored image can be erased by another reading-in. Absence of qualification during this time can be likened to a serious defect.

It is best to carry out a simultaneous scrutiny of the two opposite faces of the strip by alternating processing of image signals of successive portions of one face with processing of image signals of successive portions of the other face.

It is then possible to display the retained stored images of portions of one of the faces on a display unit which is different from that used for displaying the stored images of portions of the other face. Another purpose of the invention is to provide an equipment to perform the process defined above.

This goal is reached by an equipment of the type including at least a light-sensitive device which generates recurrently analog signals imaging successive portions of the surface of the strip and a device for processing analog signals for sensing anomalous variations of the signal level values.

The equipment, according to the invention further includes:
- an addressable mass storage to store signals for reading in each image converted by the light-sensitive device;
- a processing device which comprises: an analog-to-numerical converter for converting the analog signals denoting each image in numerical form by splitting-up the image into image elements each of which is associated a numerical value; a numerical filter for receiving the numerical signals denoting each image and for sensing the relative variations of the numerical values of the image elements; and an analyzing circuit connected to the numerical-filter output for possibly generating for each image, a defect-sensing signal in terms of the variations of the sensed numerical values;
- means for controlling the preservation of a read-in image at the end of the time during which this image was converted by the light-sensitive device, in response to the presence or absence of a defect-sensing signal corresponding to said image; and
- a display unit being connected to a mass memory for displaying a fixed image, retained in storage so as to provide a visual check of the image this represents.

The numerical filter comprises a contour-sensing two dimensional filter including means for associating with each image element a numerical information calculated in terms of the numerical values associated with adjacent image elements; the scanning circuit then includes means for generating a quantitative information derived from sensing of image elements for which the associated numerical information oversteps an initial preset threshold, and means of comparison for generating a defect-sensing signal when said quantitative information oversteps a second preset threshold.

The numerical filter may also include an edge-sensing filter for sensing the edge positions of the strip and to provide the data denoting the differences between the edge-sensed position and reference positions. The analyzing circuit acts upon these data when the sensed differences overstep a preset threshold.

The mass storage can be an analog storage for storing analog signals denoting each image. The mass storage is addressable image by image. For an analog storage at least one magnetic video-disc may be used.

Reading-in and out are respectively controlled in response to reception of defect-sensing signals. The mass storage should preferably include two memory units one of which operates in the write mode whereas the other operates in the read mode, or conversely; in this way, a stored image in a given unit is displayed whereas each new formed image is stored in the other unit.

By preference, in order to achieve a simultaneous inspection of both faces of the strip, the equipment comprises a first and a second light-sensitive device on each side of the strip for generating individual analog signals denoting the images of successive portions of a face of the strip, a switching circuit connected between, on the one hand, the light-sensitive devices and, on the other, the mass storage and the processing system, and the means for controlling the switching circuit for transmitting alternately to the mass memory and to the processing system an analog video signal for one face and an analog video signal for the other face. Two separate display units may then be used for displaying the retained stored data relating respectively to one of the faces of the strip and to the other face.

Space consideration dictates that the light-sensitive devices may have to be offset along the inspection line. In this case the video signals generated by the device ahead are delayed to make good the offset so as to have available at all times video signals relating to the opposite face of the selfsame strip section.

Other valuable features of the process and equipment according to the invention will be evinced on reading the following description, merely for information but not limitatively, with reference to the appended drawings on which:

DETAILED DESCRIPTION OF THE INVENTION

Figure 1:
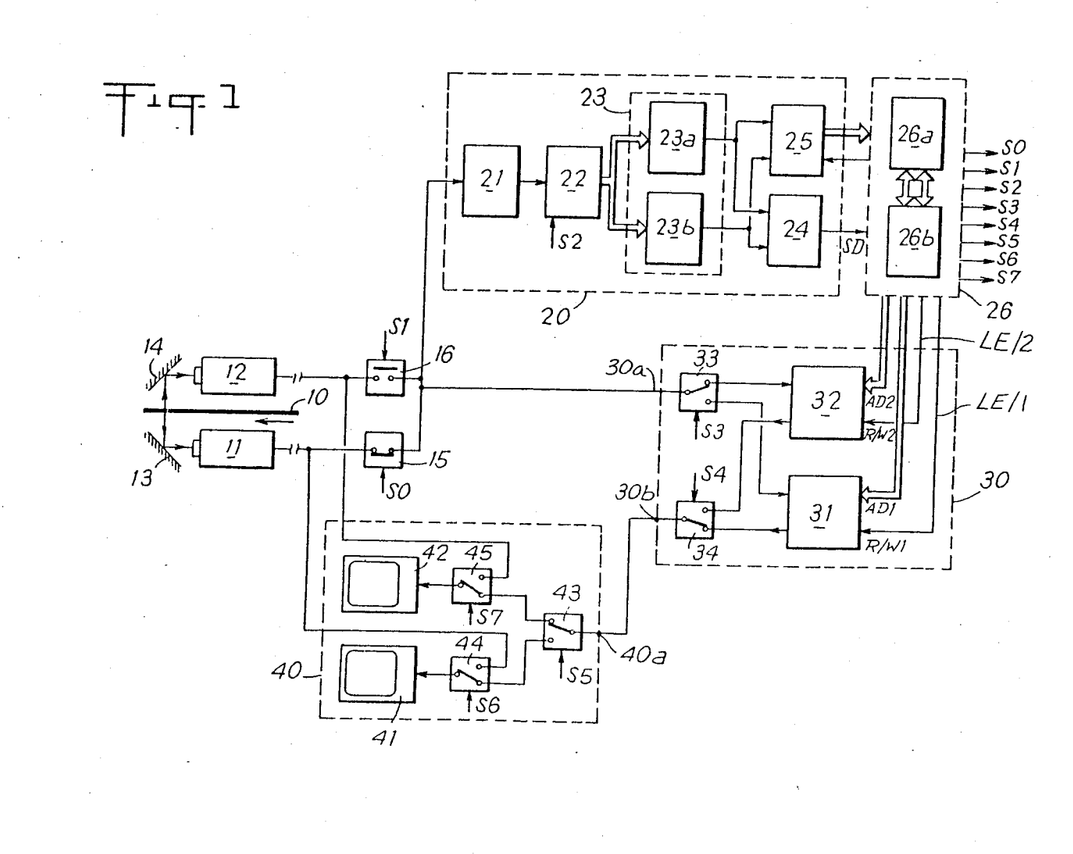
FIG. 1 is a functional diagram of the embodiment of an equipment according to the invention.

The equipment shown on FIG. 1 is designed for sensing surface defects on strip 10 while strip 10 is in motion, e.g., a strip emerging from a pickling line after hot rolling.

Each side of the strip 10 is scanned by a television camera designated respectively as 11, 12. The cameras are located on either side of the conveyance level of the strip 10 and are arranged, in the illustrated example, parallel to the strip. The images of the strip 10 are reflected back to the cameras by the mirrors 13, 14 tilted through an angle of 45° in relation to the strip. The cameras and associated mirrors and are housed in a dust-proof casing provided with an observation window on the side of the strip. This casing is itself housed in an enclosure provided with means, such as neon tubes and diffuser to illuminate the strip as consistently as possible.

Both cameras 11 and 12 are fitted with a highly sensitive tube provided with blanking capability, e.g., the tube known as ISOCON and manufactured by the British Company "English Electric Valves". This tube can be blanked electronically, thereby dispensing with electromechanical devices which are less reliable and can affect sensitivity adversely. With such a tube, the read time is 20 ms and the time exposure is adjustable. In the application considered, this exposure time is preset so as to provide adequate illumination without impeding unduly the viewing of surface unevennesses. By way of information, an exposure time of 300 μs may be suitable for a strip moving at the rate of 6 m/s, as the strip runs over approximately 2 mm during that time. Each camera is fitted with a remote-controlled lens for focusing, setting the diaphragm and the magnification ratio. The exposure speed is determined, in terms of the lens angle of the camera, so as to form successive images denoting the adjacent portions of each face of the strip, with no space-in-between consecutive portions; it is best to have a slight overlap between adjacent portions to make sure that no area escapes scanning.

Assuming that the lens angle of each camera extends over a strip length of one meter and that the going-past rate is 6 m/s, exposure speed for each camera is therefore at least equal to 6 exposures per second. As mentioned further on, the signals denote images of successive portions of both faces of the strip and are interspersed so as to be processed sequentially. Accordingly, cameras 11 and 12 operate alternately and the whole duration of exposure and reading for each image received by a camera must be less than a half-period of the exposure; this requirement is readily met on the basis of the aforesaid figures given by way of example.

Cameras 11 and 12 operate continuously, but the signals generated by these cameras are taken alternately so as to apply to the input of the processing system 20 alternately a raster generated by camera 11 and a raster generated by camera 12. This is done by transmitting the camera output signals to the input of the device 20 via switches 15 and 16 respectively. The switches are turned on alternately, and on each occasion, for just the time needed to transmit the signals to be processed by control signals, S0, S1, respectively. In line with the figures mentioned above, both signals, S0 and S1, are in the form of rectangular pulses the duration and period of which are 20 ms and 1/6 s, respectively.

The processing system 20 comprises the gain-control and analog filtering circuit 21 receiving the serialized video signals, the sample-and-hold circuit and analogue/numerical converter 22 connected to the output of circuit 21, the numerical filtering circuit 23 connected to the output of circuit 22, the analyzing circuit 24 receiving the numerical signals generated at the output of filtering circuit 23, the storage circuit 25 and microprocessor circuit 26.

Circuit 21 includes a controlled-gain amplifier for compensating the grey-level variations of the background of the strip and a pass-band filter that inhibits all but the desired signals within the relevant frequency band.

The purpose of circuit 22 is to convert numerically analog video signals; it receives a control signal S2 which sets the sampling frequency, e.g., 5 MHz.

The numerical words generated by circuit 22 are received by the filtering circuit 23 whose purpose is to sense the variations relating to the values of the numerical words.

Figure 2:
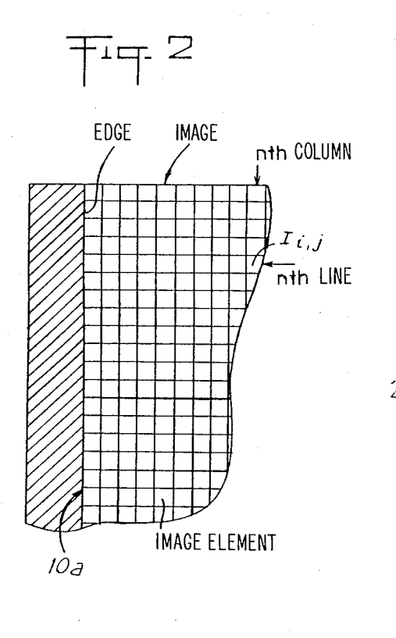
FIG. 2 illustrates operation of the numerical filter of the equipment shown on FIG. 1.

The filtering circuit comprises edge-sensing filter 23a and contour-sensing filter 23b. Referring to FIG. 2, this shows a portion of the surface of strip 10 as seen from one of the cameras. The light reflected by the surface of the strip brings about a definite contrast between both parts of the image separated by edge 10a of the strip.

The purpose of the edge-sensing filter 23a is to achieve specific processing of the signals typical of the image portion along the edges.

During an initialization phase of the process referring, for instance, to the 16 first lines of the first image, the addresses of the edges of the strip are determined, these addresses being expressed in the number of dots of a line of the raster corresponding to the edge. If designated by $I_{i,j}$ the numerical word denotes the image element located at the intersection of line i and column j. Sensing of an edge is performed by subtracting $I_{i,j+3} - I_{i,j}$, this means comparing image elements of a selfsame line which are not successive but separated by two image elements. As a variant, the differences $I_{i,j+2} - I_{i,j}$ or $I_{i,j+4} - I_{i,j}$ could be subtracted. The background transition of each side of the strip being sensed corresponds to the left-hand edge 10a of the strip. The address j+3 is stored together with the amplitude of this transition. Sensing of the other edge of the strip is achieved when a transition of the same amplitude is measured; the address of this second transition is stored. This process is continued in the same way for the 16 first lines and the transition addresses stored for each edge are averaged. These mean values make up the reference addresses for the edges A1 and A2 expressed as number of dots on a line.

Figure 3:
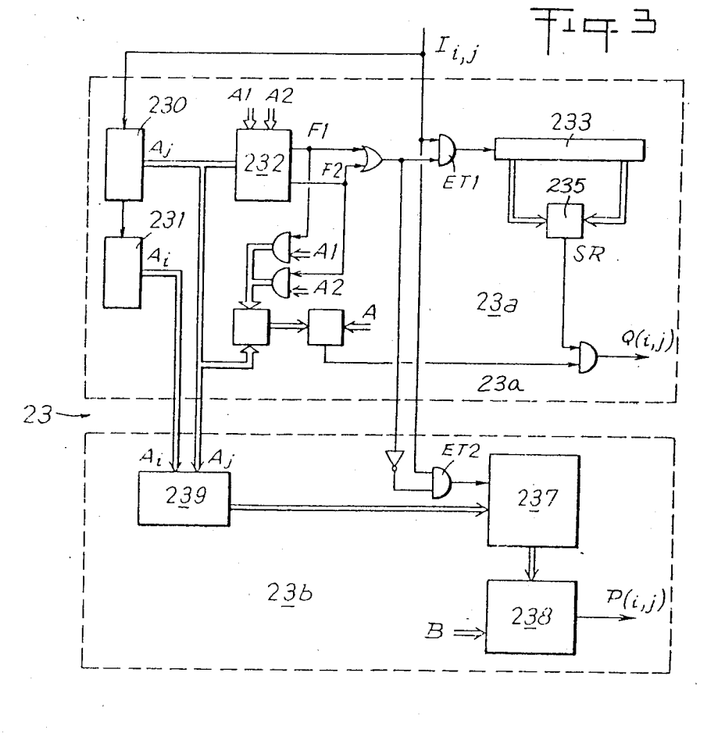
FIG. 3 is a more comprehensive drawing of the FIG. 2 numerical filter.

As FIG. 3 shows, the successive numerical words received by circuit 23 are counted by counter 230 which delivers address j of the image element corresponding to the numerical word received. At the end of each image line, (that is, when 256 numerical words have been counted), counter 230 reverts to its initial state and another analog counter 231 is incremented, this second counter providing the address i of the image element corresponding to the numerical word received. Filter 23a operates only in the image area along the edges of the strip, that is, on the image bands extending from A1−N to A1 and A2−N to A2+N. For instance, N=16 may be selected. the operating ranges of filter 23a are defined by logic circuit 232 receiving the values A1, A2, and the contents $A_j$ of counter 230 and delivering signal F1 when $A1 - N \leq A_j \leq A1 + N$ and signal F2 when $A2 - N \leq A_j \leq A1 + N$. Signals F1 and F2 are brought together by an OR gate to control opening of gate ET1 through which the numerical words received are sent to a register 233, with serial input and parallel outputs to store continuously the words denoting four successive image elements of a selfsame line. Subtractor 234 is connected to the outputs of register 233 for subtracting the difference $I_{i,j+z} - I_{i,j}$ and delivers signal SR in response to sensing of a transition corresponding to an edge. Subtracter 234 works out the difference between $A_j$ and either of values A1 or A2. Either one of these values is sent to subtracter 234 by control signals F1 and F2. This difference $A_j - A1$ or $A_j - A2$ is compared as absolute value to a preset threshold A by a comparator 236 which associates with each numerical word $I_{i,j}$ a binary value Q(i,j) equal to 1 or to 0, according to whether Q(i,j)>A or Q(i,j)≦A. Every time an edge is sensed (signal SR), the value Q(i,j) is sent to scanning circuit 24. This value will only be equal to 1 if the difference between the address of the sensed edge and the reference address is greater than B, signifying the presence of an edge defect. A value corresponding, for instance, to four image elements may be selected for B.

Beyond the operating ranges of filter 23a, the numerical words $I_{i,j}$ are processed by contour-sensing filter 23b whose function is to sense the variations indicating presence of a surface unevenness whose contour (or perimeter) is thus determined. Various types of contour-sensing filters are known in the prior art; for instance, a Prewitt two-dimensional filter: may be used. To every image element converted as a numerical word a numerical quantity in terms of the numerical words denoting the adjacent image elements is associated. For each image element, the associated quantity, according to Prewitt's formula is: $P(i,j)=[PX]+[Py]$ with $$Px=I_{i-1,j+1}+I_{i,j+1}+I_{i+1,j+1}-I_{i-1,j-1}-I_{i,j-1}-I_{i,j-1}-I_{i+1,j-1}$$

$$Py=I_{i+1,j-1}+I_{i+1,j}+I_{i+1,j+1}+I_{i-1,j-1}-I_{i-1,j}-I_{i-1,j+1}$$

This amounts to calculating, for every image element, on the one hand, the difference between the accumulated numerical words of the three adjacent image elements of the following line and the accumulated numerical words of the three adjacent image elements of the previous line and, on the other hand, the difference between the three adjacent image elements of the following column and the accumulated numerical words of the three adjacent image elements of the previous column, and then, summing these differences. When the quantity P(i,j) oversteps a preset threshold B, the image element considered is at the boundary of two comparatively different grey-level areas and, therefore on the contour of a "spot"; i.e., or surface unevenness. It should be noted that the bidirectional nature of the filter enables the sensing of contours oriented in any direction. P(i,j) is given a binary value, for instance, 1 or 0, according to whether P(i,j)>B or P(i,j)≦B.

As FIG. 3 shows, the numerical words $I_{i,j}$ to be processed by circuit 23b are sent to addressable register 237 via gate ET2, which is opened when the inverted control signal to gate ET1 is activated. Computing circuit 238 is connected to register 237 to receive from the latter the data required for calculating P(i,j). These data are read out from register 237 and controlled by the address signals delivered by addressing logic circuit 239, which receives the contents $A_j$ and $A_i$ from counters 230 and 231, that is, the address (i,j) of the image element corresponding to the word received. The quantity Px and Py and P(i,j) are generated while the numerical word $I_{i,j}$ is displayed. A comparator is provided in computing circuit 238 to compare [Px]+[Py] with threshold B so as to provide quantity P(i,j) in binary form.

The analyzing circuit 24 receives the binary signals Q(i,j) and P(i,j) generated by filters 23a and 23b, whereupon the sum S is effected for the complete image. This sum is compared with threshold C and the scanning circuit generates the defect-sensing signal SD when S≧C and does not generate a signal when S≦C. The sum S is stored in memory 25 at the same time.

Contour-sensing can be further improved by removing isolated dots, that is, by disregarding the quantities P(i,j) which overstep threshold B when the quantities associated with adjacent image elements do not overstep this threshold. The same may occur for edge sensing.

Full processing of video signals by circuits 21 to 25 is performed in real time for each image, that is, before displaying the signals typical of the following image. The data rate is very high; it may reach 1.5 million numerical words per second at the converter output. Accordingly, numerical processing is performed by wired logic so that the processing rate may be very fast. Microprocessor circuit 26 carries out such tasks as controls and linkings with outplant systems, as will be described further on. It should be noted that circuit 26 delivers the position-control signals S0 and S1 for switches 15 and 16.

As regards contour sensing, it has been merely considered above to determine the summed quantities P(i,j) which give some information as to the overall area of the defects. It should be noted that the algorithms known per se could be used for also calculating the perimeter of the defects, as well as Euler's number (countours within another contour). Should the quantities P(i,j) be used for computing the overall perimeter of the defects, it is this perimeter (and not the area, as previously) which is compared with a predetermined threshold to control transmission of a defect signal.

In conjunction with processing of analog signals typical of each image storage of such signals is performed. A storage system 30, which is used for this purpose, receives at its input 30a the output analog signals from switches 15 and 16 and storage system 30 includes two storage units 31,32 fitted with image-by-image addressable magnetic video-discs. The signals fed in are stored in either unit 31,32, according to the position of switch 33, which is fitted with a moving contact connected to input 30a and to fixed contacts connected respectively to the inputs of units 31,32. The stored signals may be read in either unit 31 or 32 according to position of switch 34, which is fitted with two fixed contacts respectively connected to the read outputs of units 31,32, and a moving contact connected to output 30b of the storage unit.

Storage units 31,32 are controlled by the signals generated by microprocessor 26. Operation in either write or read mode is controlled by additional signals L/E1 and L/E2, so that, in all instances, one of these units operates in the write mode while the other operates in the read mode. In addition, circuit 26 transmits to unit 31,32 the address signals AD1, AD2, which define the read or write addresses of the image signals and an address corresponding to this image. The circuit 26 also delivers signals S3, S4 which control the position of switches 33 and 34.

The equipment shown in FIG. 1 comprises display unit 40 of which the input 40a is connected to output 30b of the storage system The system 40 is designed to display the fixed images stored in units 31, 32. In the example shown, it comprises two television monitors 41,42, respectively, associated with both faces of strip 10. According to whether the video signals read out from the storage system 30 represent the image of a portion of the lower surface or a portion of the upper surface of the strip, these signals are routed to monitor 41 or monitor 42 via switch 43. These monitors enable also, if required, to directly display both faces of strip 10 when the strip is in motion. Accordingly, the output signals of cameras 11,12 are applied to the fixed contacts of switches 44,45 whose other fixed contacts are respectively connected to the fixed contacts of switch 43 and whose moving contacts are connected to the video inputs of monitors 31,32. Thus, according to the position of switches 44,45, either the fixed images read out from storage 30 or, the direct images of the faces of the strip in motion are displayed. Positions of switches 43,44, 45 are controlled by signals S5, S6, S7 generated by the microprocessor circuit 26.

The equipment described above operates as follows:
The signals typical of each image formed by cameras 11, 12 are scanned by processing system 20, while being stored in one of the analog storage units, to an address specified by circuit 26.

Should circuit 24 generate no defect-sensing signal SD, there is no need to retain the stored image and to take into account the data stored in storage 25. The signals typical of the following image are then stored at the same address of the same analog storage unit and the surface-unevenness data relating to the following image are stored in storage 25 instead of the previous data.

If, conversely, a defect-sensing signal SD is generated, the data stored in storage 25 is transferred to the read/write storage 26a in the microprocessor circuit and the video signals stored in the storage unit are retained, either by reversing operation of both storage units (so that the signals relating to the following image are stored in the other storage unit), or by incrementing the write address (so that the signals relating to the following image are stored at an another address in the selfsame storage unit).

Reading out from the storage unit and operation of display unit 40 are controlled by the microprocessor device so that an operator may display as fixed images all the images which were retained in the storage units (that is, the images which gave rise to transmission of a defect-sensing signal), and qualify the displayed surface unevennesses.

Qualification of the displayed unevennesses is sent to an external computer which receives the data out from the storage 25 and stored in read/write storage 26a. Such qualification is transmitted as a code showing either it refers to a slight defector to a serious defect and, in this case, the nature of the defect (whole, fold, or indentation . . . ).

Locating approximately the defect on the strip can be carried out in several ways. The defect signal can be sent to an external computer where it is in a queue until reception of qualification, the external computer being programmed as is known per se so as to follow processing of the strip throughout, and therefore capable of locating subsequently the area of the strip which was going past cameras 11,12 at the time the defect signal was transmitted. Another method consists in identifying the strip by a jet of paint ahead of the sensing station in response to the defect signal. Yet another method, the going-past speed of the strip being known, consists in generating and associating with the qualification data a coordinate information computed by measuring the time that elapsed between beginning of the process up to transmission of the defect signal.

After sending to the external computer, the particulars of the defect stored in the read/write computer 26a are erased.

The display time of the individual fixed images available for the operator is restricted, e.g., 10s. Absence of qualification at the end of this time can be likened to a serious-defect qualification.

After each qualification or every time the display time-limit ends, another image is automatically displayed from those still retained in storage units 31,32. The order of display of the images is the same as that in which they were stored. Control of the queue is achieved by microprocessor 26b in circuit 26 as well as routing of the images read out to either monitor 41 or 42 according to whether these images relate to the lower or the upper face of the strip. When there remains no image in standby in the storage units, switches 44 and 45 are controlled so as to connect monitors 41 and 42 directly to the outputs of cameras 11 and 12, respectively.

Figure 4:
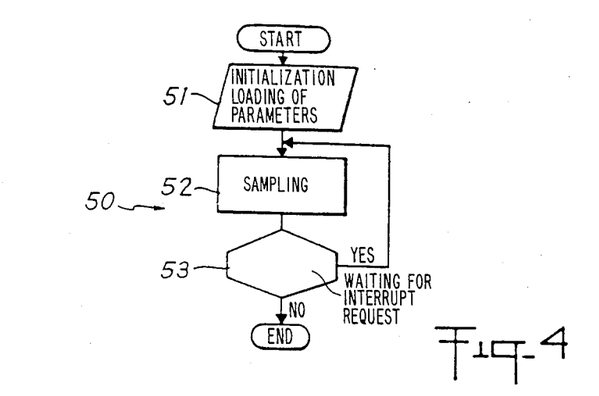
FIG. 4 is a functional flowchart of the tasks accomplished by the microprocessor of the equipment illustrated on FIG. 1.

FIG. 4 is a functional flowchart of the tasks performed by the microprocessor in circuit 26.

The main program 50 includes:

initialization and loading of parameters (step 51), (including strip speed, queue . . . ).

sampling and speed frequency stage (52), consisting in generating signals S2 at preset frequency and generating signals S1 and the signals controlling the shooting rate of cameras 11 and 12 to a frequency depending on the going-past rate, and test (53) for the interrupt request: should the response be positive, whereupon the beginning of stage 52 is reverted to; or, should the response be negative? If yes, the program is ended.

Every interrupt initiates running of a subroutine; in the order of priorities the interrupts provided for herein are those brought about by transmission of a defect signal (60), operator's action for qualifying a defect (70), end of the display time limit for a fixed image (80) and a request for dialogue with an external computer to which the microprocessor circuit is connected (90).

Reception of a defect sensing-signal brings about blocking of any other interrupt (step 61), storage of the defect particulars through read-out of the storage contents 24 and transfer into read/write storage 26a (step 62). Should the queue not be filled (test 63), either the storage units are changed over or the stored address is incremented (step 64). The change-over consists in causing the storage unit that operated in the read-in mode to operate, in the read-out mode and in causing the other storage unit to operate in the read-in mode with fast return to the initial read or write address; such change-over is only possible if an image is not being read-out of the other storage unit; otherwise, the incrementation carried out consists in gating the stored data at the following address without changing over operation of the storage units, that is, in this instance, when reading in the writing mode, move forward the videodisc by one track. The next step (65) consists in updating the queue of the stored images, calling into execution the read and time-limit subroutines, respectively, and in gating the unmasking of the interrupts. The read subroutine initiates display of the images at the address specified in the storage unit opeating in the read mode, the time-limit subroutine initiating the operator's time-limited image-viewing. Should the result of test 63 be positive, (filled queue), the subroutine proceeds directly to step 65.

In response to the interrupt brought about by the operator (step 71), while making possible an interrupt due to reception of a defect sensing-signal, the evaluation (or defect qualification) is acquired by the microprocessor (step 72). Next, an interrupt request is sent to the external computer (step 73) and either the storage units are changed over or the address is incremented in the read mode in order to read the following retained image (step 74). The read and time-limit sub-programs are respectively activated (step 75) and the queue is updated and unmasking of the interrupts is gated (step 76).

In response to the interrupt brought about by end of the display time-limit of an image, and while making possible the interrupts brought about by reception of a defect-sensing signal or to the operator's action (step 81) the initial defect of the queue is validated and a request is made to interrupt the dialog with the external computer (step 82); should the operator fail to qualify within the prescribed time-limit serious defect is perceived;

Next, either a change-over of the storage unit is proceeded with or the address is incremented in the read mode (step 83); the read and time-limit sub-routines are respectively activated (step 84) if the queue is not empty, whereupon the queue is updated and unmasking of the interrupts is gated (step 85).

In response to the interrupt brought about by a dialog request with the external computer, while making possible the other interrupts mentioned above (step 91), the defect qualification and numerical information characterizing it, which are read out of storage 25, are sent to the external computer (step 92) and unmasking the interrupts is gated (step 93).

Sending to the external computer the particulars of all the surface unevennesses sensed and the qualification given to such unevennesses have been considered above. A variant can be sending to the external computer only the particulars of surface unevennesses qualified as serious defects.

Selection between changing over the storage units and address incrementation when in the read or write mode is carried out as follows: on an initial defect being detected after the initialization step the storage units are changed over by reversing switches 33 and 34 (signals S3 and S4) and reversing L/E1 and L/E2 to display at once the relevant image and, during that time, store in the other storage unit the images to be retained, if any. After displaying this initial image, and as the first storage unit is empty, the storage units are changed over so as to display the image (if any) stored in the other unit. When there remains, in this other unit, no image to be displayed, another change over will be performed, and so forth. As long as no image is retained, or where there are none to be displayed, switches 44 and 45 are controlled (signals S6 and S7) so as to display directly the faces of the strip in motion.

The queue of images to be displayed is controlled by microprocessor: 26b, and includes, for each such image, storing its address, and a binary information showing that this image represents a portion of the lower or upper face of the strip. This binary information coincides with the condition of one of the signals, S0 and S1, respectively. When displayed, the binary information thus stored is used for controlling switch 43 (signal S5) so as to route the video signals to the relevant monitor.

It is to be understood that various changes may be made to the embodiment of the process and equipment according to the invention without detracting from the scope of the invention as defined by the appended claims.

That is how, in particular, the typical signals of each image can be read into a numerical storage, these signals being either transmitted numerically by the light-sensitive devices or transmitted in analog and digitized. The numerical storage may consist of two magnetic discs similar to those described above.

We claim:

1. In a process for sensing surface defects on a moving strip, images of successive portions of the surface of the strip being formed, the images being converted to analog signals for sensing surface light reflection variations, the process comprising the steps of:
   storing the analog signals of each image in an image storage means;
   processing the analog signals, relating to each image during the time the particular image is formed, the processing step including:
   (a) Converting the analog signals to numerical signals by splitting the image into elements, each of the elements being associated with a numerical value;
   (b) Filtering the numerical signals to sense variations relating to the numerical values of the image elements, the filtering of the numerical signals being carried out, at least in part, by sensing between adjacent image elements variations of numerical values greater in amplitude than an initial preset threshold;
   (c) analyzing the filtered numerical signals for determining whether or not a defect-sensing signal in terms of the variations sensed is to be transmitted;
   (d) retaining the image as data in the storage means in response to the transmission of the defect-sensing signal;
   reading out all retained stored data; and
   displaying the read-out retained stored data for a long enough time to allow a visual check of each of the images represented by the retained stored data.

2. A process according to claim 1, wherein the analyzing of the filtered signals step comprises:
   generating for each image, from the sensed variations having amplitudes greater than the initial threshold, quantitative information of surface unevenness of the image; and
   delivering a defect-sensing signal if the quantitative information is greater than a second preset threshold.

3. A process according to claim 1, wherein the processing step comprises:
   separating the numerical signals into first and second numerical signals, the first numerical signals being representative of image portions along edges of the strip and the second numerical signals being representative of other image portions of the strip, the first numerical signals being processed for sensing amplitude variations corresponding to a change-over from a first side to a second side of the edges of the strip and to provide information representing the difference between the sensed position of an edge of the strip and a reference position, the second numerical signals being processed for associating with each element information representing amplitude variations of numerical signals associated with adjacent image elements.

4. A process according to claim 1, wherein the processing step comprises:
   storing the analog signals representative of each image in an addressable image by image analog memory, the changeover from a first address to a second address in the analog memory being controlled in a write mode in response to the defect-sensing signal.

5. A process according to claim 1, wherein the reading out step comprises:
   reading out the retained stored data sequentially for displaying each image represented thereby during a preset time; whereby at the end of the preset time, the address of the just displayed stored image is again available in a write mode.

6. A process according to claim 1, further comprising:
   simultaneously scanning both surfaces of the strip by alternately processing images signals of successive portions of the surfaces.

7. A process according to claim 6, wherein the displaying step comprises:
- displaying the retained stored images of portions of one of the surfaces of the strip on a first display unit; and
- displaying the retained stored images of portions of the other surface of the strip on a second display unit.

8. A process according to claim 1, further comprising:
- transmitting successive images of the surface of the scanned strip directly for checking when no retained stored data of images remains to be displayed.

9. An equipment for sensing surface defects on a moving strip comprising:
- at least one light-sensitive means for generating recurrent analog signals representing images of successive surface portions of the strip;
- means for processing the analog signals for sensing anomalous surface flatness variations on the strip;
- an addressable mass storage memory means for storing signals representative of each image converted by the light-sensitive means;
- a processing means working cooperatively with the analog signal processing means and the memory means, the processing means including:
  - (a) an analog to numerical converter for converting the analog signals representative of each image numerically by splitting the image into image elements, each of the image elements being associated with a numerical value;
  - (b) a numerical filter for receiving numerical signals representing each image and for sensing relative variations of the numerical values of the image elements, the numerical filter having a contour sensing two-dimensional filter including means for associating with each image element numerical information calculated in terms of the numerical values associated with adjacent image elements;
  - (c) a scanning circuit connected to the output of the numerical filter for possibly generating, for each image, a defect-sensing signal in terms of the variations of the sensed numerical values;
- means for controlling the reading into the memory means an image to be retained at the end of the period during which the to-be-retained image was converted by the light-sensitive means, the reading being responsive to the presence of a defect-sensing signal corresponding to this image; and
- displaying means connected to the memory means for displaying as a fixed image every retained stored image, thereby providing a visual control of the images.

10. An equipment according to claim 9, wherein the numerical filter comprises:
- an edge sensing filter for sensing edge positions of the strip and for delivering data representing differences between the sensed position of the edges and reference positions.

11. An equipment according to claim 9, further comprising:
- an analyzing circuit including:
  - (d) means for generating quantitative information from the sensing of image elements for which the associated numerical information is greater than a predetermined initial threshold; and
  - (e) comparison means for generating a defect-sensing signal when the quantitative information is greater than a second predetermined threshold.

12. An equipment according to claim 9, wherein the mass storage means comprises an analog storage means for storing analog signals representing each image, the analog storage means being addressable image by image.

13. An equipment according to claim 9, wherein the mass storage means comprises at least one magnetic video disc.

14. An equipment according to claim 9, wherein the mass storage means comprises two storage units, one of the storage units operating in a write mode while the other of the storage units operating in a read mode.

15. An equipment according to claim 9, further comprising:
- control circuit means for receiving the defect-sensing signal and for controlling both writing and reading from the mass storage means.

16. An equipment according to claim 9, wherein the light-sensitive means comprises:
- first and second light-sensitive devices arranged on each side of the strip to generate analog signals representing images of successive portions of respective surfaces of the strip; and wherein the equipment further comprises:
- a switching circuit connected between the light-sensitive devices and the mass storage means; wherein the switching circuit is controlled by the controlling means for alternately transmitting to the mass memory means and the processing means analog image signals of respective surfaces of the strip.

17. An equipment according to claim 17, wherein the displaying means comprises:
- first and second display units connected to the mass memory means via switching means, the first displaying unit displaying retained stored data relating to a first surface of the strip and the second display unit displaying retained stored data relating to a second phase of the strip.

18. An equipment according to claim 17, wherein the switching means directly connects the first and second display units to respective outputs of the first and second light-sensitive devices when no retained stored images are to be displayed.

* * * * *